*(12)* United States Patent
Richman et al.

*(10)* Patent No.: US 9,086,392 B1
*(45)* Date of Patent: Jul. 21, 2015

(54) T-SENSOR DEVICES AND METHODS OF USING SAME

(75) Inventors: Bruce A. Richman, San Mateo, CA (US); Anthony Miller, San Francisco, CA (US)

(73) Assignee: ENTANGLEMENT TECHNOLOGIES, INC., Burlingame, CA (US)

( * ) Notice: Subject to any disclaimer, the term of this patent is extended or adjusted under 35 U.S.C. 154(b) by 337 days.

(21) Appl. No.: 13/567,555

(22) Filed: Aug. 6, 2012

Related U.S. Application Data

(63) Continuation-in-part of application No. 13/485,391, filed on May 31, 2012, now abandoned.

(60) Provisional application No. 61/520,111, filed on Jun. 3, 2011.

(51) Int. Cl.
*G01N 30/00* (2006.01)

(52) U.S. Cl.
CPC .................................. *G01N 30/0005* (2013.01)

(58) Field of Classification Search
CPC ................ G01N 2030/0025; G01N 2030/003; G01N 2030/203; G01N 2030/0045; G01N 30/0005
See application file for complete search history.

(56) References Cited

U.S. PATENT DOCUMENTS

| 6,541,213 B1 * | 4/2003 | Weigl et al. ..................... 435/7.1 |
| 2002/0076350 A1 * | 6/2002 | Weigl et al. ..................... 422/58 |

* cited by examiner

*Primary Examiner* — Paul West
(74) *Attorney, Agent, or Firm* — Rankin, Hill & Clark LLP

(57) ABSTRACT

T-sensor devices that include a main conduit that defines a diffusion space, at least a first and second supply conduit for conveying fluids into the main conduit, and at least one sensor having a sensing zone that extends into the diffusion space in a fixed location relative to the main conduit. The first and second supply conduits are separated by divider from which a diffusion interface extends into the diffusion space. In order to capture sensing information without employing moving the physical location of sensors or employing more sensors, devices according to the invention alter a location of a diffusion interface extending into the diffusion space from a diffusion start point on the divider relative to the sensing zone of the at least one sensor, without altering the fixed location of the sensor relative to the main conduit. Methods of sensing properties of fluids and analytes are also disclosed.

19 Claims, 9 Drawing Sheets

T-SENSOR DEVICES AND METHODS OF USING SAME

CROSS-REFERENCE TO RELATED APPLICATIONS

This application is a continuation-in-part of co-pending U.S. application Ser. No. 13/485,391, filed May 31, 2012, which claims priority to U.S. Provisional Application Ser. No. 61/520,111, filed Jun. 3, 2011.

BACKGROUND OF INVENTION

1. Field of Invention

The present invention relates to fluid T-sensors. More particularly, the present invention relates to fluid T-sensors that are capable of altering a location of a diffusion interface between at least two fluids flowing in a diffusion space within a main conduit relative to a sensing zone of at least one sensor that is fixed relative to the main conduit without altering the fixed location of the at least one sensor relative to the main conduit.

2. Description of Related Art

H-filters were developed in the late 1990's. In their simplest form, H-filters combine two or more fluid flows into a combined, side-by-side, laminar flow stream. Over the length of the filter, species in the fluids diffuse from one flow stream into another. Slow diffusing species tend to remain in the original laminar flow stream over a finite period of time, whereas fast diffusing species tend to appear or "occur" in the other laminar flow stream within the same finite period of time. In an H-filter, the streams are separated at the end of the combined flow stream, which effectively filters out or separates fast-diffusing species from slow-diffusing species without the need for membranes and other components that require cleaning or replacement.

Conceptually, a T-sensor is similar to the first half of an H-filter. Chemical detection of the diffusing species is completed in the combined laminar flow stream. Post-separation can be conducted, but is not required. Thus, a T-sensor can be considered as a simplification of an H-filter, which includes the combining T but does not require the separation T.

FIG. 1 is a schematic illustration of a basic T-sensor 10 that combines two separate input fluids flowing in the direction of arrows 20, 30, respectively, into a laminar flow shown by arrows 40 through a main conduit 50. Diffusion begins immediately after the two input fluids contact each other at a diffusion start point (time=0) 60, and proceeds perpendicular (lateral) to the flow direction over time. The lateral position is the equivalent of diffusion distance, as indicated by arrow 70. As different chemical species diffuse at different rates, they tend to stratify laterally toward the end of the filter/sensor. The longitudinal position within the filter/sensor (along the direction of flow) is equivalent to diffusion time 80 by the scale factor of (approximately) the flow rate (the horizontal dashed line 90 represents the diffusion interface between the two input fluids, and the lateral dashed lines tipped by arrows 100, 110 represent the extent to which species from one input fluid have diffused into the other input fluid). It will be appreciated that the actual equivalence is more complex since the laminar flow rate varies across the flow cross-section. Fast diffusing species spread uniformly while slow diffusing species stay mostly on their original side of the flow. Thus, the fast diffusing species occur or appear on the opposite side isolated from the slow diffusing species. This property of the filter/sensor is especially useful if one of the combined flows is a carrier fluid absent of any relevant species to be separated/detected (e.g., a "zero fluid" such as pure water or solvent, or $N_2$ gas, which could be the input fluid flowing in the direction of arrow 20 in FIG. 1) and another of the combined flows is a mixture of species to be separated/detected (e.g., a "sample", which could be the input fluid flowing in the direction of arrow 30).

As previously noted, in an H-filter the output of the lateral section of flow furthest into the carrier side of the filter is peeled off, since this portion includes primarily only the fast diffusing species. Other separation techniques can be combined with the diffusion, including electric or magnetic field gradient (polar and polarizable species tend toward the high field). These additional techniques serve to increase the selectivity of the filter/sensor.

Ideally, the number of sensing locations 120 in a T-sensor would be unlimited. An entire sensing image (in the plane of FIG. 1) would capture all times of diffusion after the diffusion start point (along the flow direction) and all distances from the initial diffusion start point on either side of the diffusion interface where the flows are joined at the input T (perpendicular to flow direction). Such an image would contain all the available information on the diffusion, subject to the species selectivity of the sensing method. However, the sensing method often is spatially sparse, for example because of resource limitations. Cavity enhanced absorption spectroscopy (CEAS), such as cavity ring-down spectroscopy (CRDS), is one example of a sensing method that is usually sparse. A separate optical cavity and associated laser beam and optics are usually needed for each spatial location (re-imaging cavities, such as double-confocal, are an exception to this general rule). The resource expense of CEAS makes desirable the effective use of only one or a small number of CEAS cavities. Despite this resource expense and limitation to sparse sampling, CEAS offers extremely high sensitivity allowing for the detection of trace analyte concentrations.

Normally, the entrance apertures of each fluid to be combined in a T-sensor are fixed. Thus, the pressure of the fluid incident on its aperture (relative to the other fluids) and the size of its aperture determine the relative flow from that fluid. A limited number of sensing locations and fixed apertures results in a loss of information compared with the entire image sensing.

BRIEF SUMMARY OF THE INVENTION

The present invention provides fluid T-sensors that are capable of altering a location of a diffusion interface between at least two fluids flowing in a diffusion space within a main conduit relative to a sensing zone of at least one sensor that is fixed relative to the main conduit without altering the fixed location of the at least one sensor relative to the main conduit. Embodiments of the invention include T-sensors comprising a time-varying set of apertures that are able to move in lateral and/or longitudinal positions, thereby allowing fixed sensors to capture some or all of the lost sensing image information. A slow variation simply modulates the lateral location of diffusion interface without significantly affecting the mapping of diffusion time onto the flow-longitudinal coordinate. A fast variation modulates a combination of the diffusion interface and diffusion time (e.g. when longitudinal diffusion is comparable with the modulation spatial period). Further embodiments of the invention include T-sensors comprising one or more flow control valves that are in fluid communication with one or more of the supply conduits, a data receiver and a controller that is operatively associated with the flow control valve, the data receiver and the at least one sensor. Adjustment of the flow rate of fluids through the T-sensors allows for adjustment of the location of the diffusion interface relative to sensors, thereby providing additional image information without altering the substantially fixed location of the sensor relative to the main conduit. T-sensors incorporating both movable dividers and flow control valves are also disclosed.

Fluid T-sensors according to the invention are particularly useful when the sensor(s) utilized therein are sensors utilized in cavity enhanced absorption spectroscopy (e.g., cavity ringdown spectroscopy). Such T-sensors comprise one or more optical cavities and associated laser beam and optics in one or more relatively fixed locations within the sensor. Variation of the apertures and/or other parameters allows the effective location of the relatively fixed sensors to be altered in the diffusion space.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
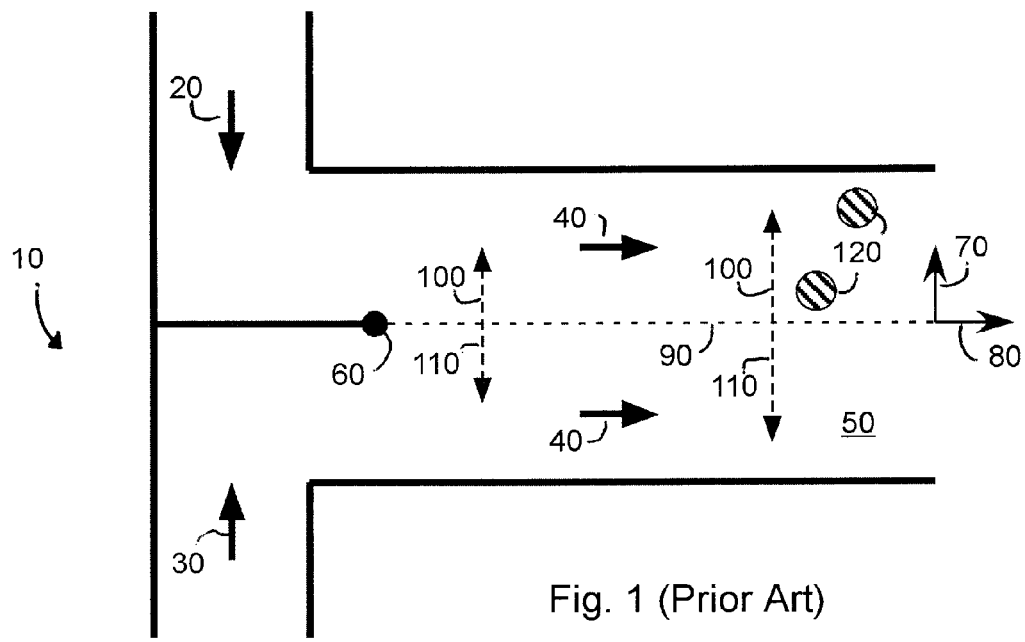
FIG. 1 is a schematic representation of a prior art T-sensor having a limited number of fixed sensing locations and joined flows with a stationary divider separating fixed apertures.
Figure 2:
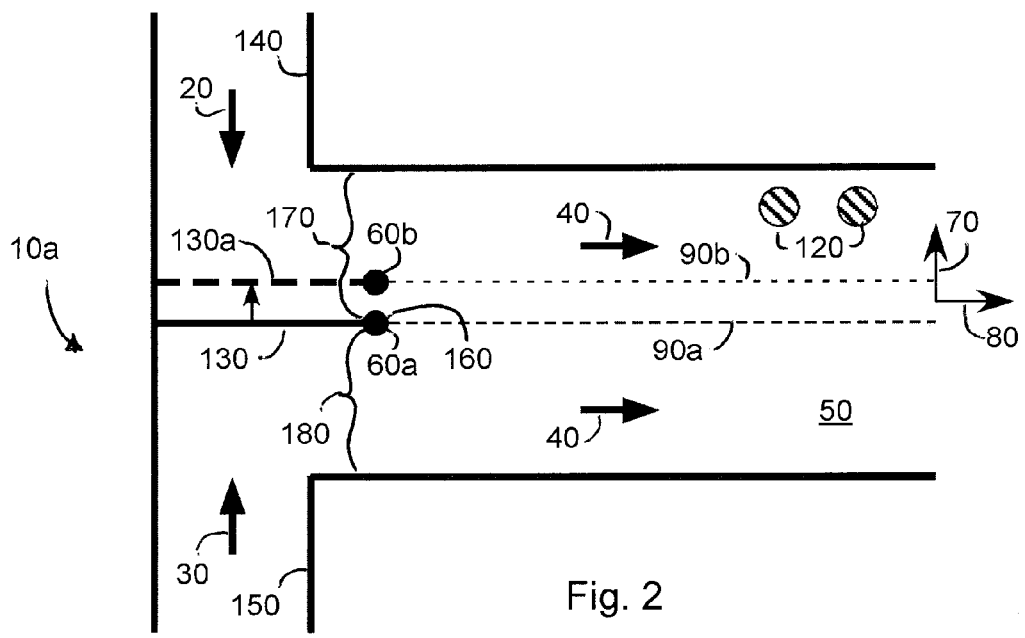
FIG. 2 is a schematic representation of a T-sensor according to an embodiment of the invention having a limited number of fixed sensing locations and joined flows with a divider that is movable laterally, but not longitudinally, thus allowing for lateral variation of the flow apertures.

FIG. 2 is a schematic representation of a T-sensor 10a according to an embodiment of the invention having a limited number of sensing locations 120 and two joined flows 20, 30 with a laterally movable but longitudinally fixed divider 130 between the two input flows (reference numbers for similar elements in the T-sensor shown in FIG. 1 also appear in FIG. 2). An input fluid (e.g., Fluid A—see arrow 20) flows into the T-sensor through a first supply conduit 140. A second input fluid (e.g. Fluid B—see arrow 30) flows into the T-sensor through a second supply conduit 150. The first fluid and the second fluid are separated from each other by the divider 130. The end of the divider 160 where the two fluids first contact each other is defined as an initial diffusion start point 60a. It will be appreciated that FIG. 2 depicts the T-sensor in only two-dimensions (i.e., the plane defined by the paper on which FIG. 2 is drawn) and thus the end of the divider 160 appears in FIG. 2 as a point. In actuality, the divider 130 will typically be a wall that extends above and/or below the plane of FIG. 2. The two fluids flow in a laminar manner through a main conduit 50 in which at least one sensor 120 is fixed. Each fluid flows through an aperture 170, 180 into the main conduit 50. Each aperture 170, 180 is defined as being the area extending from the end of the divider 160 to the nearest location on the main conduit 50. In the embodiment disclosed in FIG. 2, the full aperture (i.e., sum of the first aperture and the second aperture) is fixed, and the divider 130 between the two input flows can move to any position within the full aperture (i.e., to alter the dimensions of the first aperture and the second aperture). In FIG. 2, the divider 130 is illustrated in two positions. In a first position, the divider 130 is shown as a dark solid line separating the two input fluid flows. In the second position, the divider 130a is shown as a dashed line terminating in a laterally relocated diffusion start point (above the first position) 60b, which is deviated from the initial diffusion start point 60a.

If the flow speed of each fluid is identical, so that the flow of each is proportional to its respective aperture size, then a diffusion interface remains (approximately) at the lateral position of the division between apertures for the entire length of the main conduit sensor, and the diffusion interface will thus define a plane that includes the dashed line 90a that extends in the flow direction from the initial diffusion start point 60a in FIG. 2 and that is perpendicular to the plane in which FIG. 2 is drawn (It will be appreciated by those having skill in the art that the diffusion interface will remain substantially straight if it is located relatively far from the walls of the main conduit, but as the diffusion interface approaches the walls of the main conduit the effect of the laminar flow slows the fluid and may cause the interface to steer). If the flow densities (speeds) are not balanced as described above, then the diffusion interface will define a curved surface (rather than a planar surface) that extends in the flow direction from the diffusion start point in FIG. 2, but which is still perpendicular to the plane in which FIG. 2 is drawn. More particularly, the curved surface will start at the diffusion start point at the end of the aperture divider and bend away from the side of the main conduit receiving the higher input flow speed and toward the side of the main conduit receiving the lower input flow speed. In the example shown in FIG. 2, for ease of discussion, it may be assumed that the flow speeds of the inputs are identical so that the diffusion interface defines a plane as previously described. In this example, two sensors each having a sensing zone (depicted in FIG. 2 as a circle containing diagonal stripes) 120 are separated longitudinally (e.g. different diffusion times) and have the same lateral position (e.g. same distance from the initial diffusion interface 90a). Each sensor is capable of sensing a property of fluids and/or analytes in fluids flowing in a flow direction through the diffusion space in the sensing zone. Moving the aperture divider so that a zero fluid fills the full aperture will flush the sensor region with zero fluid. Examples of actuators to move the aperture divider include: a stepper motor, a servomotor, cam (driven by a rotary stepper or servo motor), and pneumatic actuator. The depth of the T-sensor, its dimension perpendicular to the plane of FIG. 2, is limited typically by planar walls impermeable to the fluid and parallel to the plane of FIG. 2. The movable aperture divider forms an impermeable seal to these walls, but which still allows the movement of the divider. Types of this seal include gasket material (on one or both of the wall and divider edge), and a foldable apron (e.g. a bellows) permanently sealed to both the wall (at or beyond both maximum travel extents of the divider) and the divider edge.

As noted, the sensors measure some property or properties of the fluid in the sensing zone. Examples of these properties include: optical absorption at discrete optical wavelengths or in a continuous range of wavelengths, electric or magnetic polarization (or electric susceptibility or magnetic permeability), electric conductivity, temperature, thermal conductivity, and (chemical) affinity (e.g. to a functionalized surface). The invention is particularly useful if the sensor or sensing method cannot be accomplished in an image format as is the standard method used with a T-sensor, or an image format is excessively expensive or difficult. If the sensor/sensing method is optical detection, at the current time an image format is usually unavailable for optical wavelengths outside the visible range. Examples of the sensor include: direct optical absorption (e.g. laser absorption spectroscopy), cavity enhanced absorption spectroscopy (CEAS), cavity ring-down spectroscopy (CRDS), optical emission spectroscopy (e.g. fluorescence), electronic bridge, thermocouple, and thermistor. The optical absorption spectroscopies (including CEAS and CRDS) typically use wavelengths in the UV, visible, or IR. CEAS and CRDS are described, for example, in the following references, which are incorporated by reference: Barbara A. Paldus and Alexander A. Kachanov, *Spectroscopic Techniques: Cavity-enhanced methods*, Atomic, Molecular, and Optical Physics Handbook, Part C: Molecules, 621-640, (2005); Kenneth W. Busch and Marianna A. Busch, *Cavity-Ringdown Spectroscopy: An Ultratrace-Absorption Measurement Technique*, American Chemical Society Symposium Series, 720, (1999); Giel Berden, Rudy Peeters, and Gerard Meijer, *Cavity ring-down spectroscopy: Experimental schemes and applications*, International Reviews in Physical Chemistry, 19, 4, 565-607, (2000); and Kevin K. Lehmann, *Ring-down Spectroscopy Cell Using Continuous Wave Excitation for Trace Species Detection*, U.S. Pat. No. 5,528,040. The optical cavities of CEAS and CRDS are typically 1 cm to 100 cm long, although the intersection with the T-sensor may be only 0.1 to 10 cm. The optical finesse of the cavities is typically in the range of 100 to 100,000. At least one sensor must be present in the device. But, two or more can also be utilized, if desired.

A T-sensor combines at least two fluid flows into the main conduit. Examples of fluids that can be processed through a T-sensor include liquids, gases, solutions, suspensions, and gelatins. T-sensor dimensions (in particular the width of the main conduit) typically range from microns to several centimeters. Fluid flow rates range from micro-liters per minute (e.g. for liquids in micron-size conduits) to liters per minute (e.g. for gas in cm-size conduits). The dimensions and flow rates must be consistent such that the flow is substantially laminar in the relevant volume where diffusion measurements are obtained using the sensor(s), and in particular in the volume between the end of the aperture divider and the sensor(s). Examples of materials that can be utilized to construct the T-sensor walls include glass, fused silica, metal (formed, extruded, or machined), epoxy, polymer (e.g. polymethyl methacrylate PMMA) and other materials that do not adversely interact with the fluids and/or do not adversely affect the information obtained from the sensor(s).

Some potential uses for the invention are: trace (very low concentration) gas monitoring of medium and large molecules such as ethane and larger volatile organic compounds, air pollutants, or toxic fumes; monitoring or quantification of particulates such as aerosols and soot; analyzing biological liquid samples such as chemical constituents of blood or plant extract; analyzing the gas headspace of biological samples; analyzing liquid water samples.

At the beginning of T-sensor operation, the fluids to be analyzed are prepared so as to flow into the system. The flows of the first and second fluids are initiated and the aperture divider is moved to an initial position. After a period of time has elapsed, allowing the flow conditions to reach steady state and for the conduit to be purged of other fluids (e.g., in some applications approximately one second), the sensor(s) begins recording fluid property(ies) (e.g. the optical absorption) within the sensing zone(s). The sensor output may be recorded in the controller. The controller directs the movement of the aperture divider along a prescribed path. This path causes the effective location of the sensor(s) within the diffusion process to change along a specific trajectory relative to the diffusion interface of the two fluids without moving the fixed location of the sensor(s) relative to the main conduit. The path of the aperture divider is chosen to maximize the signal available to the signal processing algorithms used in the controller. The speed of movement of the aperture divider may vary over the course of the path. The sensor records during the duration of the aperture divider movement. This procedure may be repeated to improve the measurement results or to measure new fluids.

The sensor(s) obtain information (e.g., the optical absorption of the fluid in the sensing zone) during the course of the measurement when the aperture is adjusted. Information (data) obtained by the sensor as well as information relating to the state of the aperture or flow during the measurement is transmitted to a data receiver (e.g., a memory, a display, a data analyzer etc.). The sensor output reflects an effective trajectory through the diffusion plane set by the flow conditions and aperture trajectory. Different analyte species will diffuse at different rates set by their diffusion coefficient. Due to the different diffusion, the concentrations of the analyte species contained in the fluid flows will vary along the effective trajectory of the sensor caused by the movement of the aperture divider. Both qualitative and quantitative estimations can be made based on the information obtained during operation of the T-sensor. For example, using a Bayesian estimation algorithm, the concentrations of the different analyte molecules contained in the fluid flows can be estimated. The estimator uses both the aperture divider trajectory and the optical absorption sensor outputs to calculate the species concentrations.

The signal processing procedure is the same when the fluid flows are varied. The controller records the flow rate settings as well as the fluid properties measured by the sensors to estimate the concentrations of the analyte species contained in the fluids.

If the divider between the apertures moves slowly (i.e., the speed at which the divider moves is much less than the speed of fluid flow in the main conduit), so that longitudinal diffusion is negligible (the adiabatic case), then the diffusion interface moves with the divider, and the effective diffusion distance of the sensing locations changes with it. In FIG. 2, the equivalent diffusion times of each sensing location do not change. If the division between the apertures moves rapidly (i.e., the speed at which the divider moves is not much less than the speed of the fluid flow in the main conduit), so that longitudinal diffusion is significant, then the diffusion interface changes for each sensing location and the equivalent diffusion time is a function of the sensing longitudinal location, the flow rate, and the real time (relative to the aperture movement). The particular function depends on the temporal function of the aperture movement. Two simple cases are a step function and a sinusoidal modulation.

Figure 3:
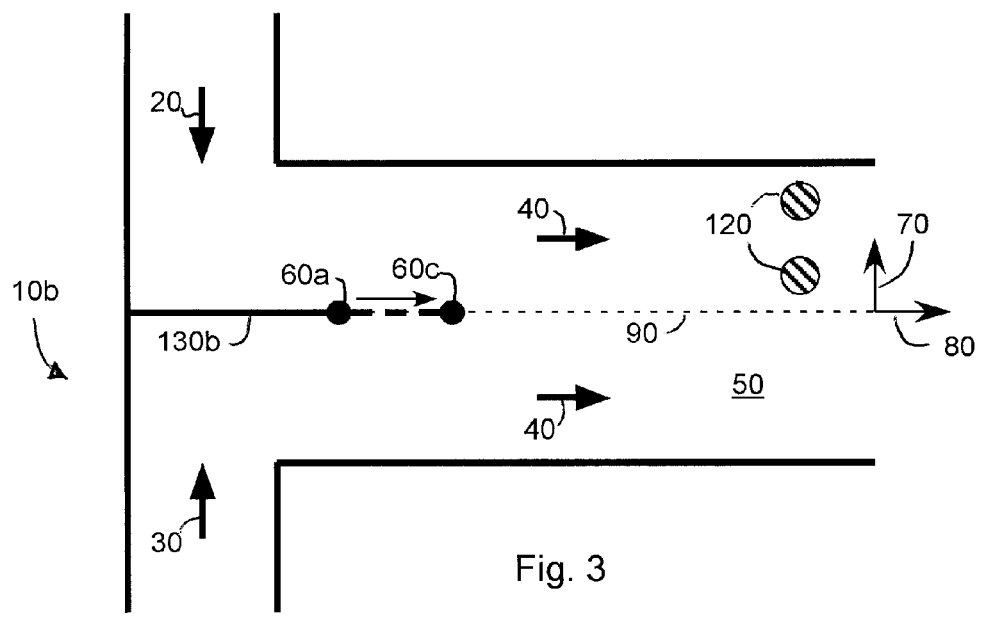
FIG. 3 is a schematic representation of a T-sensor according to another embodiment of the invention having a limited number of fixed sensing locations and joined flows with a divider that is movable longitudinally, but not laterally, thus allowing for longitudinal variation of the flow apertures.

FIG. 3 is similar to FIG. 2, at least in the sense that it is a schematic diagram of a T-sensor 10b with a limited number of sensing locations 120 and two joined flows 20, 30. However, unlike FIG. 2, which included a laterally movable divider 130 that was longitudinally fixed, the T-sensor 10b shown in FIG. 3 is fitted with a longitudinally movable, but laterally fixed divider 130b. The divider 130b between the two input flows can move upstream as far as the mechanical design will allow, and downstream as far as of the sensing location(s), thereby relocating longitudinally the diffusion start from an initial diffusion start point 60a to a longitudinally relocated diffusion start point 60c. For simplicity, assume that the flow density of each fluid is identical, so that the flow of each is proportional to its aperture size, and the diffusion interface 90 remains at the lateral position of the division between apertures for the entire length of the main conduit 50 of T-sensor 10b (It will be appreciated by those having skill in the art that the diffusion interface will remain substantially straight if it is located relatively far from the walls of the main conduit, but as the diffusion interface approaches the walls of the main conduit the effect of the laminar flow slows the fluid and may cause the interface to steer). In this example, the two sensing locations 120 are separated laterally (e.g. different diffusion distances) and have the same longitudinal position. If the sensors are on the zero fluid side of the T-sensor, then moving the aperture divider up to the sensors will flush the sensor region with zero fluid.

If the divider between the apertures moves slowly (the adiabatic case), then the effective diffusion time origin of the interface moves with the division, and the effective diffusion time of the sensing locations changes with it. The equivalent diffusion distances of each sensing location do not change.

If the division between the apertures moves rapidly, but not as rapidly as the flow rate, then the flow rate needs to be included in the determination of the effective diffusion time (similar to a delayed field potential). If the divider movement overtakes the flow rate, then the diffusion is partial and cut off in the overtaken length. Then both equivalent diffusion distance and equivalent diffusion time at each sensing location are complex functions of real time relative to the aperture movement and the flow rate, and the sensing location. Normally, the complexity caused by this rapid divider movement is undesirable.

Figure 4:
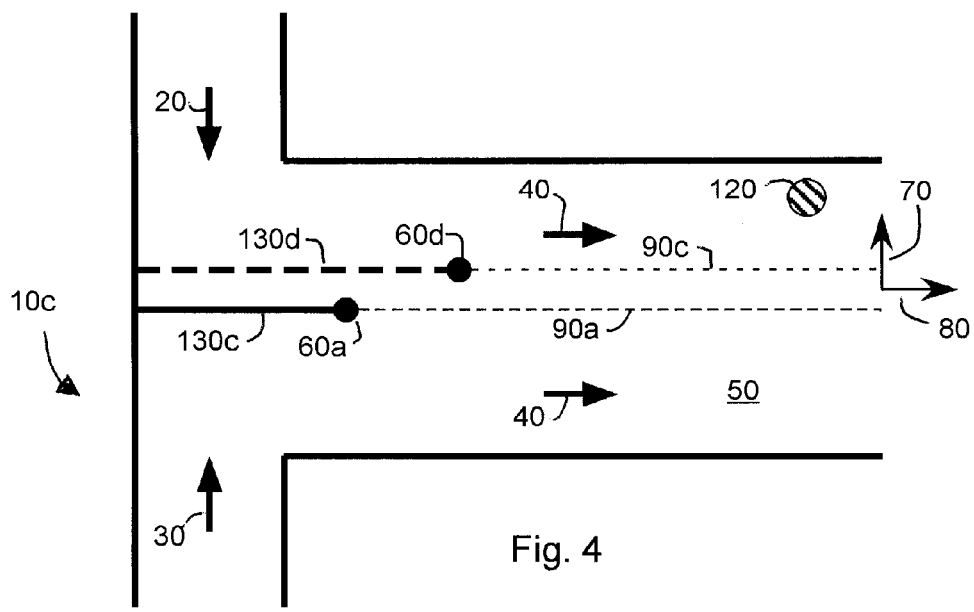
FIG. 4 is a schematic representation of a T-sensor according to another embodiment of the invention with one fixed sensing location and joined flows with a divider that is movable laterally and longitudinally, thus allowing for lateral and/or longitudinal variation of the flow apertures.

FIG. 4 is a schematic diagram of a T-sensor that incorporates the movable divider features of the T-sensors shown in FIGS. 2 and 3. The T-sensor shown in FIG. 4 is provided with one sensing location 120 (although two or more could be utilized, if desired) and two joined flows 20, 30 with a laterally and longitudinally movable divider 130c between the input flows. The divider 130c between the two input flows 20, 30 can move upstream as far as the mechanical design will allow, and downstream as far as of the sensing location 120. As in the FIGS. 2 and 3, the divider 130c is illustrated in two positions (i.e., a first position as a solid line segment terminating in a diffusion start point 60a and as a second position as a dashed line segment terminating in laterally and longitudinally relocated diffusion start point 60d). For simplicity, assume that the flow density of each fluid is identical, so that the flow of each is proportional to its aperture size, and the diffusion interfaces 90a, 90c remain at the lateral position of the division between apertures for the entire length of the sensor (It will be appreciated by those having skill in the art that the diffusion interface will remain substantially straight if it is located relatively far from the walls of the main conduit, but as the diffusion interface approaches the walls of the main conduit the effect of the laminar flow slows the fluid and may cause the interface to steer). Scanning the flow aperture divider through its lateral-longitudinal space, simultaneously scans the effective diffusion distance and diffusion time of the sensing location, thus creating an image equivalent to the instantaneous image acquired with an unlimited number of sensors as described above in the second paragraph. Conveniently, any region of the complete image can be acquired by scanning the aperture divider over its corresponding limited space. This allows more rapid measurements than the complete scan, which is useful if the concentration(s) of the species of interest are changing rapidly. Flushing the sensor region with zero fluid can be accomplished by moving the aperture divider either so that the zero fluid fills the entire T-sensor aperture (as in FIG. 2) or so that the divider is up to the sensor (as in FIG. 3), or a combination of both motions.

Figure 5:
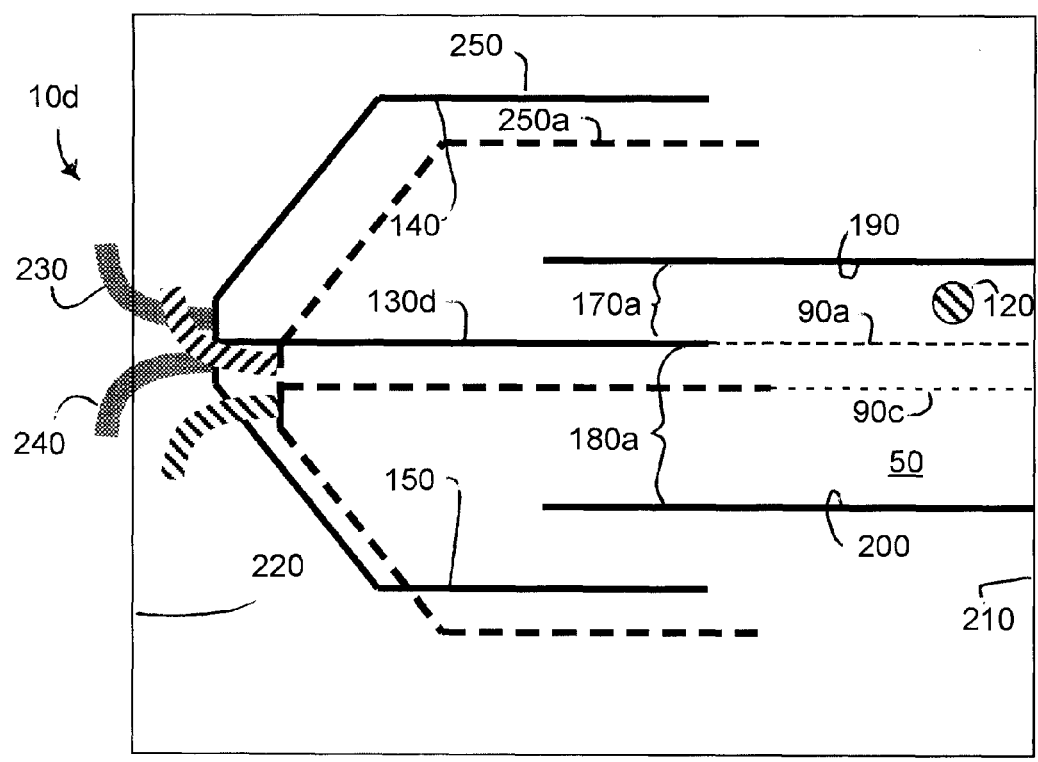
FIG. 5 is a schematic representation of a T-sensor according to another embodiment of the invention that permits repositioning of the aperture divider in both directions, laterally and longitudinally relative to the main conduit containing a fixed sensor.

FIG. 5 shows schematic implementation of T-sensor 10d with free motion of the divider 130d in both directions, laterally and longitudinally, relative to the fixed walls 190, 200 of the main conduit 50. The width of each supply conduit 140, 150 is (at least) the same width (or greater) than the width of the main conduit 50, and the width of the T-sensor floor and ceiling are at least sufficient to permit the divider 130d to be positioned approximately adjacent to each of the walls 190, 200 defining the main conduit 50. These dimensions ensure that the flows are fully contained over the full range of motion of the aperture divider. The floor and ceiling of the output side 210, and the top and bottom edges of the walls of the input side 220 can be lined with Teflon® to seal the flows and reduce friction. Flow density remains constant across each input aperture 170a, 180a including pieces within and without T-sensor output aperture. This helps to ensure that the flows into the T-sensor output section track properly (scale as sub-aperture size) as aperture divider moves. The excess flows that do not enter the T-sensor output aperture flow freely away and can be collected so as not to interfere with the T-sensor. A translation actuator can attach to the input aperture assembly near the input tubes 230, 240. The main conduit containing the sensor is fixed relative to the floor and ceiling sandwiching the assembly containing the divider and supply conduit walls. But the assembly containing the divider and supply conduit walls can be moved laterally and/or longitudinally relative to the main conduit to vary the apertures and the diffusion interface extending into the main conduit from the diffusion start point relative to the sensing zone of the sensor. In FIG. 5, the movable portion of the T-sensor 10*d* is shown in solid lines in a first position 250, and in dashed lines in a second position 250*a*. The initial diffusion interface 90*a* occurs when the movable portion T-sensor 10*d* is in the first position 250, and the laterally and longitudinally relocated diffusion interface 90*c* occurs when the movable portion T-sensor 10*d* is in the second position 250*a*. Thus, the location of the diffusion interface can be relocated relative to the sensing location 120 in the main conduit 50.

It will be appreciated that T-sensors according to the invention can comprise more than two supply conduits. For example, a T-sensor according to the invention could further comprise at least a third supply conduit for conveying a third fluid through a third aperture into the main conduit. In such an instance, the second supply conduit and the third supply conduit would be separated from each other proximal to the second aperture and the third aperture by a second divider. And, a second plane that includes a line parallel to the flow direction and which also passes through the main conduit, the second supply conduit, the third supply conduit, the sensing zone and the second divider would include a second diffusion start point defined by an end of the second divider between the second aperture and the third aperture. As in the case of the T-sensors previously disclosed, the second diffusion start point would be movable in the second plane relative to the sensing zone of the sensor so as to alter an effective location of the at least one sensor in the diffusion space without altering the fixed location of the sensor relative to the main conduit. It is conceivable that T-sensors could employ more than three supply conduits.

Figure 6:
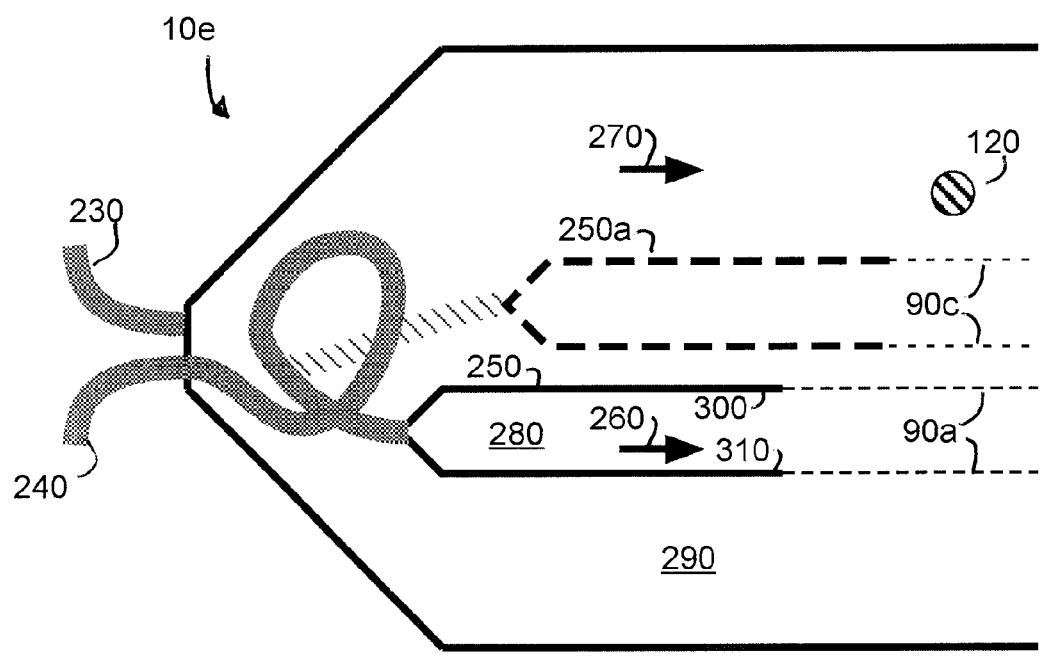
FIG. 6 is a schematic representation of a T-sensor according to another embodiment of the invention in which an inner flow is completely contained within an outer flow, and the inner flow can be translated laterally and longitudinally relative to the sensor main conduit containing a fixed sensor.

FIG. 6 shows a more complex diffusion alternative to the T-sensor 10*e* than shown in FIG. 5, but with potentially reduced mechanical complexity. An inner flow shown by arrow 260 is completely contained within an outer flow shown by arrow 270. An inner flow channel 280 is translated within the plane of the Figure within the outer flow channel 290, thus changing the diffusion time and distance at the sensor 120, but there are now two initial diffusion interfaces 90*a*, at each side 300, 310 of the inner flow channel 280 (each side of the inner flow channel acts as a divider between the flows). Flow density remains constant across each input aperture (outer and middle), which ensures that the total flows of each input remain unchanged as the inner channel moves (translates position). The translation actuator can be completely inside the outer flow channel.

Figure 7:
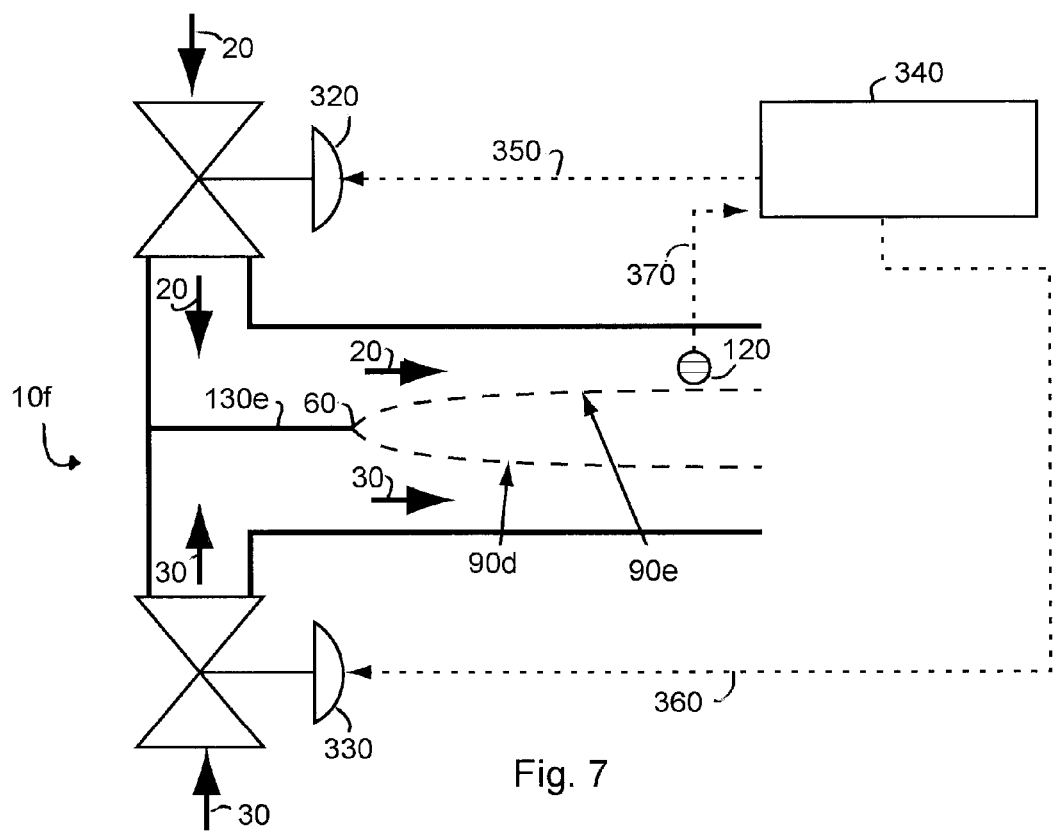
FIG. 7 is a schematic representation of a T-sensor according to another embodiment of the invention in which variation of a diffusion interface relative to a fixed sensor is altered by adjustment of the relative flow rates of the fluids.

Moving the divider between the flows is only one method to change the effective location of fixed sensors in the 2-dimensional diffusion space relative to the diffusion interface. Varying the fluid flow rates at the input to the T-sensor has a similar effect. In particular, if both input flows are equal and increased together, then the diffusion time at the fixed sensors decreases; it behaves as the reciprocal to the input flow rates. The diffusion interface remains at the lateral position of the division between apertures for the entire length of the sensor. As shown in FIG. 7, if one input flow (shown by arrows 20) increases and the other input flow (shown by arrows 30) decreases such that the total flow remains constant, then the diffusion interface begins at the end-point 60 of the aperture divider 130 and downstream it curves away from this lateral position toward the side with lower flow. Two diffusion interfaces are shown in FIG. 7, the first diffusion interface 90*d* occurs when input flow 20 is greater than input flow 30, and the second diffusion interface 90*e* occurs when input flow 20 is less than input flow 30. It asymptotically approaches a new lateral position that divides the T-sensor total aperture proportionally to the two input flows. FIG. 7 schematically illustrates a T-sensor 10*f* in which electronic flow control valves 320, 330 in operative communication (e.g., valve control signals 350, 360) with suitable system control and data processing 340 can be adjusted to adjust the flow of at least one of, and preferably both of, the fluids as to alter a location of a diffusion interface extending into the diffusion space from the diffusion start point relative to the sensing zone of the at least one sensor without altering the fixed location of the sensor relative to the main conduit while communicating information relating to the flow control valve and sensor (e.g., sensor output data 370) to the data receiver within the system control and data processing 340. The diffusion interface is shown in two locations (both dashed lines extending from the diffusion start point), but it will be appreciated that depending upon flow conditions the diffusion interface will exist in only one location, which can be varied relative to the sensing zone of the sensor.

Varying each input flow independently is a combination of varying them together and varying them oppositely, so that the fixed sensor(s) have access to a large portion of the 2-D diffusion space. The fixed sensors in this embodiment with fixed divider and variable flows cannot access the full diffusion space that can be accessed with the movable divider. However, it can be more reliable than the movable aperture embodiment since it lacks moving parts within the T-sensor itself. The absence of a movable seal is especially advantageous.

Figure 8:
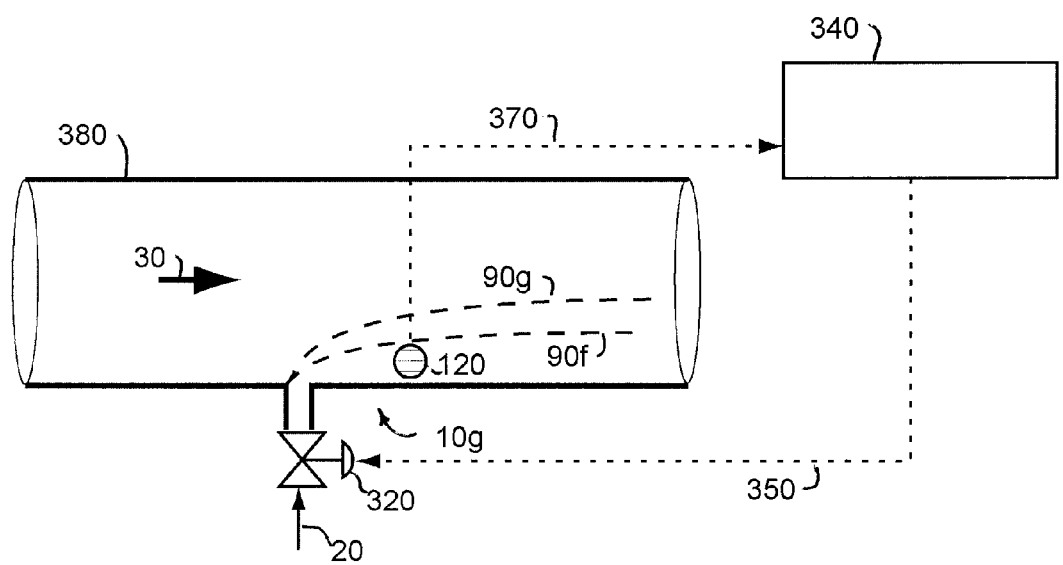
FIG. 8 is a schematic representation of a variable flow implementation in which a fluid is injected, with variable flow, into a stream of sample fluid flowing through a main conduit containing a fixed sensor.

FIG. 8 shows an embodiment of the variable flow implementation in which zero fluid (shown by arrow 20) is injected, with variable flow, into a stream of sample fluid flowing through a pipe or conduit 380. The injection forms the equivalent of a T-sensor. The dashed lines indicate the paths of the diffusion interface (e.g. the boundary between the two fluids in the absence of diffusion) for slow 90*f* (nearest the wall of the sample tube) and fast 90*g* (farthest from the wall of the sample tube) injected zero fluid flow. Varying the flow rate of the zero fluid into the sample stream changes the relative position of the diffusion interface with respect to the fixed sensor. If the flow rates of both the zero fluid and the sample fluid are varied, then both the diffusion distance and diffusion time at the sensor can be controlled.

Figure 9:
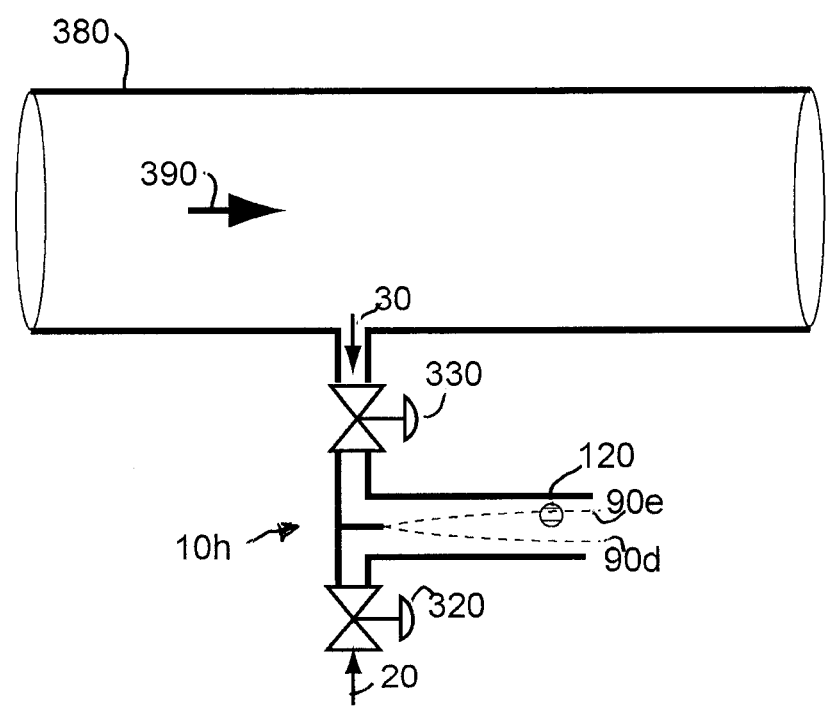
FIG. 9 is a schematic representation of a variable flow implementation in which fluid is extracted from a main flow through a T-sensor in which variation of a diffusion interface relative to a fixed sensor in a main conduit is altered by adjustment of the relative flow rates of the fluids.

FIG. 9 shows an embodiment of the T-sensor 10*h* using any combination of movable aperture and variable flow. The sample fluid shown by arrow 30 is drawn from a process fluid stream 390 flowing through a pipe 380 or other conduit, and its flow into the T-sensor 10*h* is controlled by a flow regulation device 330. The flow 30 from the process fluid stream 390 is combined with a zero fluid stream shown by arrow 20, and controlled by valve 320. The diffusion interfaces 90*d*, 90*e* relative to a fixed sensor 120 can be varied by moving the aperture divider and/or by varying flow rates, as discussed above. Although not depicted in FIG. 9, the flow control valves and/or the divider position can be controlled by a controller, which also receives and processes data from the sensor.

Figure 10:
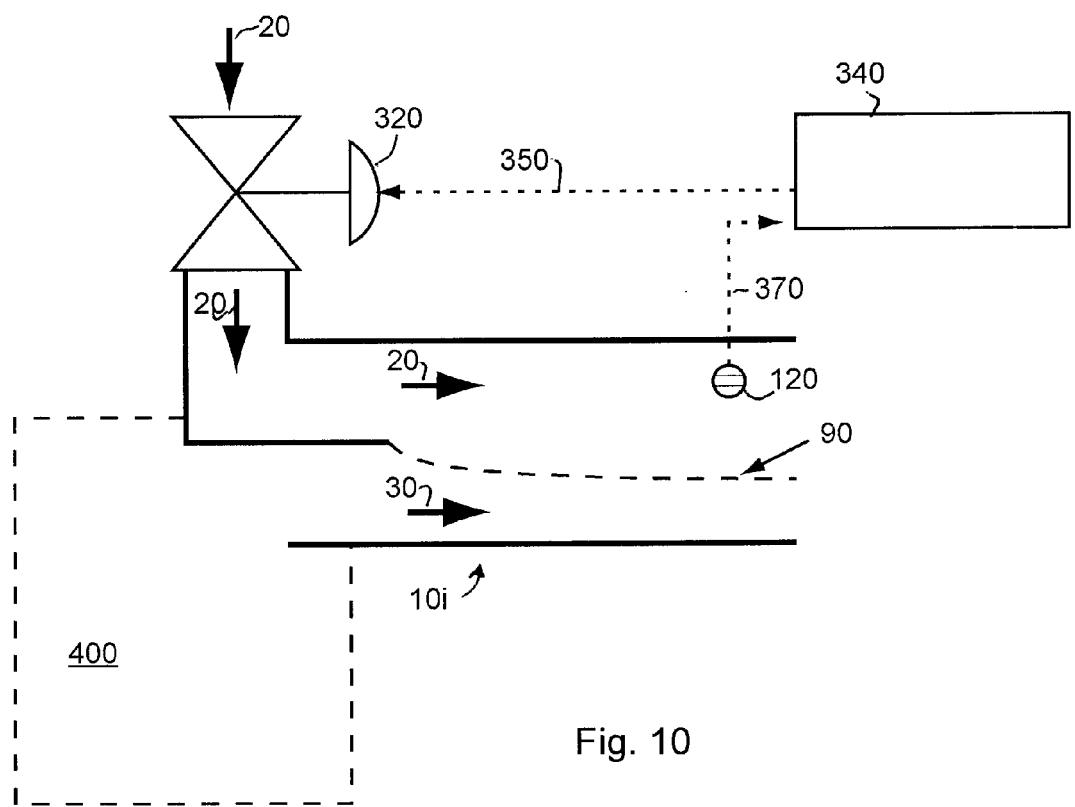
FIG. 10 is a schematic representation of a T-sensor according to another embodiment of the invention in which the Venturi-effect is utilized together with an adjustable flow rate to vary the location of a diffusion interface relative to a fixed sensor.
Figure 11:
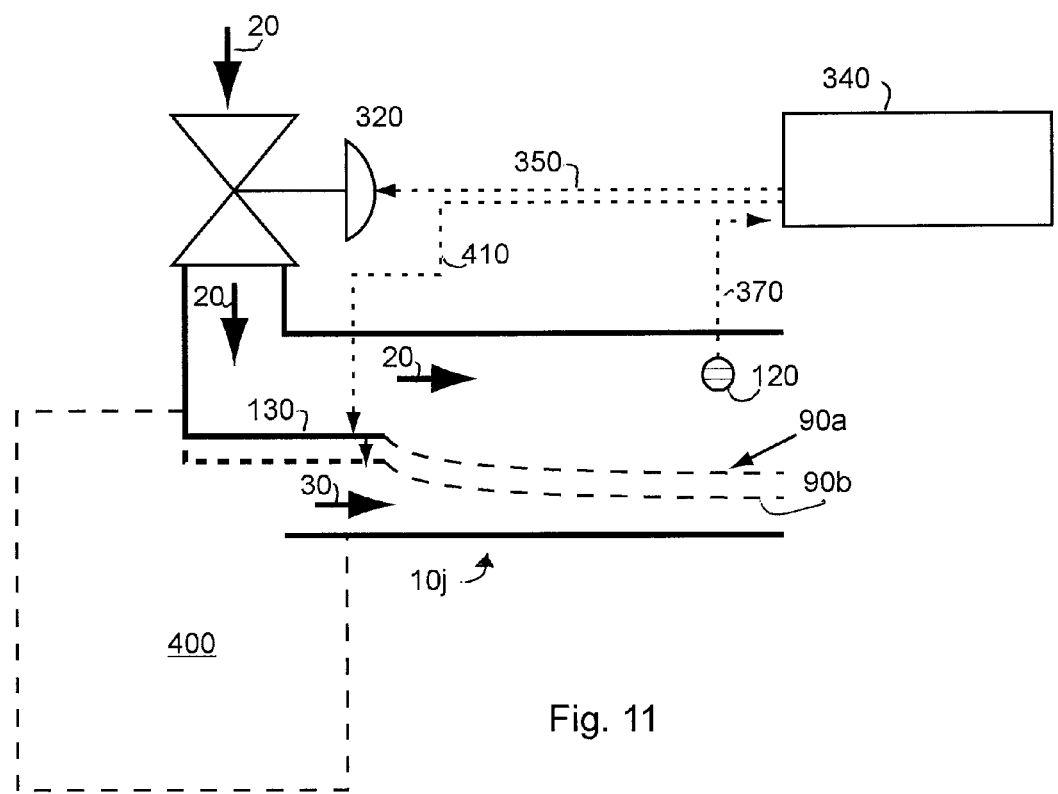
FIG. 11 is a schematic representation of a T-sensor according to another embodiment of the invention in which the Venturi-effect is utilized together with an adjustable flow rate and an adjustable divider so as to vary the dimensions of the apertures and to vary the location of a diffusion interface relative to a fixed sensor.

Another specific embodiment of the invention uses the Venturi effect. As shown in FIG. 10, a flow of zero fluid shown by arrows 20 in the upper channel draws sample fluid 30 (e.g., from atmosphere 400) into the lower channel by the Venturi effect. The flows approximately retain the same ratio as the zero fluid flow is changed, thus changing the diffusion time at the fixed sensor 120. Laterally moving the divider 130 between the channels, as shown in FIG. 11, changes the diffusion distance at the fixed sensor 120. A divider position signal 410 can be sent to the controller 340. A combination of variable zero fluid flow and movable divider provides the fixed sensor with access to a large portion of the 2-D diffusion space including potentially the full range of diffusion distance. Moving the divider longitudinally provides access of all diffusion times to the fixed sensor, just as it does in the exemplary T-sensors shown in FIGS. 3 and 4.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A T-sensor device comprising:
a main conduit that defines a diffusion space;
a first supply conduit for conveying a first fluid through a first aperture into the main conduit;
a second supply conduit for conveying a second fluid through a second aperture into the main conduit; and
at least one sensor having a sensing zone that extends into the diffusion space in a fixed location relative to the main conduit, the sensor being capable of sensing a property of fluids and/or analytes in fluids flowing in a flow direction through the diffusion space in the sensing zone;
wherein the first supply conduit and the second supply conduit are separated from each other proximal to the first aperture and the second aperture by a divider,
wherein a plane that includes a line parallel to the flow direction and which also passes through the main conduit, at least a portion of the first supply conduit, at least a portion of the second supply conduit, the sensing zone and at least a portion of the divider includes a diffusion start point defined by an end of the divider between the first aperture and the second aperture, and
wherein the diffusion start point is movable in the plane relative to the sensing zone of the sensor so as to alter a location of a diffusion interface extending into the diffusion space from the diffusion start point relative to the sensing zone of the at least one sensor without altering the fixed location of the sensor relative to the main conduit.

2. The T-sensor device according to claim 1 wherein the end of the divider is movable in the plane laterally relative to the flow direction so as to alter width dimensions of the first aperture and the second aperture.

3. The T-sensor device according to claim 1 wherein the end of the divider is movable in the plane parallel to the flow direction without altering width dimensions of the first aperture and the second aperture.

4. The T-sensor device according to claim 1 wherein the end of the divider is movable in the plane both laterally relative to the flow direction and longitudinally parallel to the flow direction.

5. The T-sensor device according to claim 4 wherein the main conduit is received within the first aperture and the second aperture such that the divider extends into the main conduit, and wherein the first supply conduit, second supply conduit and divider are movable as a unit together relative to the main conduit.

6. The T-sensor device according to claim 1 wherein the first supply conduit is disposed entirely within the second supply conduit, and wherein the first supply conduit is movable in the plane laterally relative to the flow direction and/or longitudinally parallel to the flow direction.

7. The T-sensor device according to claim 1 wherein the first supply conduit, the second supply conduit and the main conduit are microfluidic channels.

8. The T-sensor device according to claim 1 wherein the at least one sensor is an optical sensor.

9. The T-sensor device according to claim 8 wherein the optical sensor is a cavity ring-down spectrometer.

10. The T-sensor device according to claim 1 further comprising at least a third supply conduit for conveying a third fluid through a third aperture into the main conduit, wherein the second supply conduit and the third supply conduit are separated from each other proximal to the second aperture and the third aperture by a second divider, wherein a second plane that includes a line parallel to the flow direction and which also passes through the main conduit, the second supply conduit, the third supply conduit, the sensing zone and the second divider includes a second diffusion start point defined by an end of the second divider between the second aperture and the third aperture, and wherein the second diffusion start point is movable in the second plane relative to the sensing zone of the sensor so as to alter an effective location of the at least one sensor in the diffusion space without altering the fixed location of the sensor relative to the main conduit.

11. A T-sensor device comprising:
a main conduit that defines a diffusion space;
a first supply conduit for conveying a first fluid through a first aperture into the main conduit;
a second supply conduit for conveying a second fluid through a second aperture into the main conduit;
a flow control valve in fluid communication with the first supply conduit for adjusting the flow of the first fluid through the first supply conduit;
at least one sensor having a sensing zone that extends into the diffusion space in a fixed location relative to the main conduit, the sensor being capable of sensing a property of fluids and/or analytes in fluids flowing in a flow direction through the diffusion space in the sensing zone;
a data receiver; and
a controller operatively associated with the flow control valve, the data receiver and the at least one sensor;
wherein the first supply conduit and the second supply conduit are separated from each other proximal to the first aperture and the second aperture by a divider, and
wherein a plane that includes a line parallel to the flow direction and which also passes through the main conduit, the first supply conduit, the second supply conduit, the sensing zone and the divider includes a diffusion start point defined by an end of the divider between the first aperture and the second aperture,
wherein the controller is configured to adjust the flow of the first fluid through the first supply conduit via the flow control valve so as to alter a location of a diffusion interface extending into the diffusion space from the diffusion start point relative to the sensing zone of the at least one sensor without altering the fixed location of the sensor relative to the main conduit while communicating information relating to the flow control valve and sensor to the data receiver as the sensor is sensing the property of fluids and/or analytes in fluids flowing in the flow direction through the diffusion space in the sensing zone, and
wherein the data receiver is configured to combine the information communicated by the controller relating to the flow control valve and sensor at a plurality of flows to determine a diffusion property of fluids and/or analytes in fluids flowing in the flow direction through the diffusion space in the sensing zone.

12. The T-sensor device according to claim 11 further comprising a second flow control valve in fluid communication with the second supply conduit for adjusting the flow of the second fluid through the second supply conduit, wherein the controller adjusts the flow of the second fluid through the second supply conduit via the second flow control valve while communicating information relating to the second flow control valve and sensor to the data receiver.

13. The T-sensor device according to claim 12 wherein first supply conduit is connected to a pipe such that the flow control valve is disposed between the pipe and the first aperture.

14. The T-sensor device according to claim 11 wherein the second supply conduit and the main conduit together define a pipe to which the first supply conduit is connected.

15. The T-sensor device according to claim 14 wherein the second supply conduit and the main conduit are integrally formed.

16. The T-sensor device according to claim 11 wherein first supply conduit is connected to a pipe such that the flow control valve is disposed between the pipe and the first aperture.

17. The T-sensor device according to claim 11 wherein an end of the second supply conduit opposite the second aperture is open to the atmosphere and flow of the second fluid into the main channel is effectuated via the Venturi effect.

18. The T-sensor device according to claim 17 wherein the diffusion start point is movable in the plane relative to the sensing zone of the sensor so as to alter an effective location of the at least one sensor in the diffusion space without altering the fixed location of the sensor relative to the main conduit.

19. The T-sensor device according to claim 18 wherein the end of the divider is movable in the plane laterally relative to the flow direction so as to alter width dimensions of the first aperture and the second aperture.

* * * * *